United States Patent [19]

Miller

[11] 4,195,075
[45] Mar. 25, 1980

[54] METHOD AND DEVICE FOR CONTROLLING INSECTS ON LIVESTOCK

[75] Inventor: William V. Miller, Modesto, Calif.

[73] Assignee: Shell Oil Company, Houston, Tex.

[21] Appl. No.: 944,513

[22] Filed: Sep. 20, 1978

[51] Int. Cl.$^2$ ............................................. A01K 13/00
[52] U.S. Cl. ...................................... 424/14; 424/16; 424/28; 424/78; 119/156
[58] Field of Search ...................... 424/14, 16, 28, 78, 424/83; 119/106, 156, 159

[56] References Cited

U.S. PATENT DOCUMENTS

| | | | |
|---|---|---|---|
| 3,731,414 | 5/1973 | Murphy et al. | 40/301 |
| 3,812,859 | 5/1974 | Murphy et al. | 128/330 |
| 3,852,416 | 12/1974 | Grubb et al. | 424/14 |
| 3,904,746 | 9/1975 | Aries | 424/28 |
| 3,942,480 | 3/1976 | Hair et al. | 119/156 |
| 4,062,968 | 12/1977 | Fujimoto et al. | 424/275 |

OTHER PUBLICATIONS

Harris, R. L. et al., Chem. Abstr., 87 #113034d, (1977), of Southwest Entomol, 1976, 1(4), 194–197, "Control of Tabanids on Horses".

Barlow, F. et al., Chem. Abstr., 87 #162731n, (1977), of Pestic. Sci., 1977, 8(3): 291–300, "Some Laboratory Investigations Relevant to the Possible Use of New Pyrethroids in Control of Mosquitoes and Tsetse Flies".

Nolan, J., Chem Abstr., 88 #33129u, (1978), of Pestic. Sci., 1977, 8(5), 484–486, "Resistance to Synthetic Pyrethroids in a DDT-Resistant Strain of Boophilus Microplus".

Primary Examiner—Shep K. Rose

[57] ABSTRACT

Cattle and other livestock are protected from insects such as face flies, horn flies, ticks and the like by use of a uniquely effective insect control device attached to the animal. The insect control device comprises a polymeric resin matrix, preferably in the form of an ear tag or ear band, containing a liquid, insecticidally-active isomer of alpha-cyano-3-phenoxy-benzyl-alpha-isopropyl-4-chlorophenyl acetate.

11 Claims, No Drawings

METHOD AND DEVICE FOR CONTROLLING INSECTS ON LIVESTOCK

BACKGROUND OF THE INVENTION

This invention relates to a method and device for controlling harmful insects on cattle and other livestock. More particularly it relates to a control device which when attached to the animal's ear, not only controls insects over the head and neck portion of the animal, but provides control over essentially the entire body for extended periods of time.

It is well known that livestock are frequently troubled by various types of insects such as face flies, horn flies, lice, mosquitoes, ticks, etc., which prey upon them causing irritation and sometimes infection of the skin, eyes and ears. This not only results in interference with the animal's normal feeding and grazing habits, but can result in serious illness or even death of the animal, since insects are often carriers of infectious diseases.

In the past a number of methods have been proposed to combat this serious problem. Unfortunately, however, most of these methods have proved less than satisfactory in one or more aspects as discussed below.

One conventional method involves manually treating each animal with an insecticide spray. This method of treatment however is prohibitively expensive when large numbers of animals are involved or when the animals are allowed to graze over a wide area.

Other conventional methods rely on self-application of the insecticide by the animal. These methods typically involve placing an insecticide dispensing device such as "dust bags" or oilers in areas frequented by the animals so that they will come into contact with them, whereupon some of the insecticide will be transferred from the dispensing device to the animal. While these self-application techniques are less time-consuming than individual manual treatment, they are also less reliable since the animal might only infrequently come into contact with the insecticide dispensing devices, and even then the amount of insecticide transferred to the animal might be insufficient, or be unevenly distributed, resulting in incomplete protection.

Another more recently developed technique for controlling insects on livestock is based on the application of slow release pesticide technology to this problem. It is known in the art that slow release pesticide generators can be prepared by mixing certain pesticides with a resinous substance which releases the insecticide over an extended period of time. Such "slow-release pesticidal generators" are described, for example, in U.S. Pat. No. 3,318,769 and U.S. Pat. No. 3,944,662.

Generally the pesticides selected for use in such generators fall into one of two classes: volatile insecticides, such as 2,2-dichlorovinyl dimethyl phosphate (DDVP) and 1,2-dibromo-2,2-dichloroethyl dimethyl phosphate (Naled), which are released from the resinous substance as a vapor and (2) non-volatile insecticides which crystallize from the resinous substance under typical use conditions. Representatives of this latter class of insecticides are 2-chloro-(2,4,5-trichlorophenyl)vinyl dimethyl phosphate (stirofos) and 1-naphthyl methylcarbamate (carbaryl) which are commercially employed in pet collars and tags, as are DDVP and naled.

The application of slow-release pesticidal generators to the control of insects in livestock is disclosed in U.S. Pat. No. 3,765,200 and U.S. Pat. No. 3,942,480 which describe two different insect control devices attachable to the animal ears for the control (repelling) of ticks. The only insecticide specifically disclosed in these patents, however, is the volatile insecticide DDVP. It is also mentioned in U.S. Pat. No. 3,942,480 that all known chemical repellants used for incorporation in plastic material have a relatively short useful life extending not much beyond two to three months thus necessitating the replacement of the insecticide-containing device at relatively short intervals.

The object of the present invention is to provide an insect control device which can be used to effectively control a variety of insect pests including flies (e.g., face flies, horn flies, stable flies, etc.), ticks, lice and mosquitoes on cattle and other livestock for extended periods of time, i.e., up to an entire season, without the need for replacement. "Livestock" as this term is used in the present specification and claims is intended to include cattle, sheep, swine, goats and horses.

SUMMARY OF THE INVENTION

It has now been found, and forms the basis for the present invention that a certain non-volatile, non-crystallizing, insecticide can be incorporated into a polymeric resin matrix to form an insect control device which when attached to cattle and other livestock releases sufficient insecticide to provide effective control of a variety of insect pests over a sustained period of time. This finding is particularly surprising in that from the physical properties of the insecticide alone, it would not be expected that the insecticide would be released from a resinous matrix, and indeed laboratory tests confirmed that there is no significant release of insecticide either by volatilization or crystallization under in vitro conditions. However, in spite of these findings, it was discovered that when the insecticide-containing resinous matrix was attached to the ear of an animal, that sufficient amounts of insecticide are released to obtain highly effective control of the insect pests such as face flies, horn flies and ticks over extended period of time. The reason why the insecticide is released from the resinous matrix under field conditions, but not under laboratory conditions, is not precisely known. However, it is theorized the oils, fats and/or waxes which are secreted within the ears of the animal or elsewhere on the body serve to extract or solubilize the insecticide dispersed in the resinous matrix thereby effecting its release. Once the insecticide is released it is apparently distributed by the natural grooming habits of the animal to other parts of its body, thereby providing the outstanding control observed in field tests.

DETAILED DESCRIPTION OF THE INVENTION

The insecticide which is utilized in the method and insect control device of the present invention is alpha-cyano-3-phenoxybenzyl-alpha-isopropyl-4-chlorophenyl acetate, which can exist in a number of stereoisomeric forms having varying insecticidal activity. The physical state of the stereoisomers can also vary from a liquid to a crystalline state depending on the particular stereoisomer(s) present and the method of preparation. For purposes of the present invention, any liquid, insecticidally-active stereoisomer or combination of stereoisomers of alpha-cyano-3-phenoxybenzyl-alpha-isopropyl-4-chlorophenyl acetate can be employed. Preferably, the insecticide utilized will contain at least 10 percent by weight (%w) of the stereoisomer S-(−)-alphacyano-3-phenoxybenzyl S-(+)-alpha-isopropyl-4-chlorophenyl acetate. The preparation of liquid insecticidal compositions suitable for use in the present invention is described in U.S. Pat. No. 4,062,968.

The alpha-cyano-3-phenoxybenzyl-alpha-isopropyl-4-chlorophenyl acetate insecticide may comprise from about 1 to about 20%w of the total composition with concentrations of about 3 to about 15%w being preferred. When used to formulate ear tags, the optimum concentration of the insecticide is in the neighborhood of 8-10%w.

The insect control device of the present invention comprises the aforesaid insecticide dispersed in a flexible polymeric resin matrix. The device may be prepared by a variety of means depending on the substrate matrix material used. Suitable means of preparation include, for example, forming a dry blend of a thermoplastic resin, plasticizer and insecticide and using sufficient mixing and heat to bring about a homogeneous melt which can be cast, extruded or injection molded into a desired shape such as tags, bands or the like for attachment to the animal's ear or other oily, fatty or waxy part of the animal's body. Alternatively, the liquid insecticide can be absorbed into a preformed polymeric resin article containing all of the ingredients except the insecticide. Another method of preparation is to disperse the insecticide into the ingredients of a thermosetting composition, which composition subsequently can be shaped and cured. Other methods of preparation will be obvious to those skilled in the art from these examples.

In general any thermoplastic or flexible thermoset resin or elastomer which is compatible with aforementioned insecticide and is capable of releasing insecticidally effective amounts of the insecticide when exposed to any oily, fatty or waxy environment on the animal being treated can be employed as the polymeric resin matrix. The resins or elastomers can be selected by matching the Hilderbrand solubility parameter of the matrix material with that of the aforesaid insecticide. The solubility parameter of the insecticide has been estimated to be approximately 8.3 cal.$^{\frac{1}{2}}$ cm$^{-3/2}$ at 25° C. from the heat of vaporization calculated from vapor pressure/temperature measurements.

Suitable thermoplastic resins include plasticized solid polyvinyl resins where the insecticide itself is one component of the plasticizer used. Such thermoplastic resins include polyvinyl halides, such as polyvinyl chloride (PVC), polyvinyl esters, polyvinylidene chloride and chlorinated polyethylene. Plasticizers which may be employed in conjunction with the insecticide to plasticize the thermoplastic resins include esters of polybasic acids such as phthalate esters, sebacate esters, adipate esters and citrate esters. Especially preferred plasticizers include dioctyl adipate and dioctyl phthalate. In general, the plasticizer concentrations will vary from about 10 to about 45%w of the total composition, with amounts of from about 25 to about 30%w being preferred.

Suitable elastomers include hevea brasiliensis, cis-1,4-polyisoprene, polybutadiene, and chlorinated natural and synthetic rubbers; thermoplastic elastomers such as SBS (styrene-butadiene-styrene), SEPS (styrene-ethylene-propylene-styrene), CEPC (cyclohexane-ethylene-propylene-cyclohexane) and CEBC (cyclohexane-ethylene-butylene-cyclohexane), where the insecticide is capable of acting as an extending oil.

Suitable flexible thermoset resins comprise those in which the curing ingredients are selected to match the solubility parameter of the insecticide after the mass has been cured to the desired shape. Examples of such resins are the so-called polyurethanes in which a difunctional isocyanate such as toluene diisocyanate or diphenyl methane diisocyanate is cured for example with a polyhydroxyl compound (polyol) which is selected so that the mixture of the two curing agents is compatible with the insecticide. The insecticide in this case acts asn an external plasticizer and contributes to the flexibility of the device. Also useful are the epoxy resins, for example, those based on the diglycidyl ether of bisphenol A where the curing agent is a long chain polyamine or a long chain polybasic acid and where the curing ingredients are specifically chosen to act as an internal plasticizer to impart additional flexibility to the device.

Because the preferred form of the insect control device of the invention is a tag for attachment to cattle and other livestock, the polymeric resin material should be sufficiently strong, yet flexible for this purpose. For this reason and because of commercial availability and relatively low cost, plasticized thermoplastic resins are preferred, and in particular polyvinyl chloride plasticized with dioctyl adipate or dioctyl phthalate. In general, the flexible polymeric resin employed in the present insect control devices will comprise from about 35 to about 75%w of the total composition, with amounts of from about 40 to about 70%w being preferred.

Other ingredients such as stabilizers, attractants, dyes, fillers, colorants or other biocides can also be used in the present insect control device without departing from the scope of this invention. Useful additives such as carbon black, titanium dioxide and other insoluble pigments and fillers, which when added in small amounts, i.e., 1%w or less, serve to color the resinous matrix.

The insect control device of the invention can be attached to cattle or other livestock employing any of a variety of conventional attachment means. In the case of attachment to the ear of an animal the fastening means can take the form of a single element or band, one end of which is capable of piercing the animal's ear. Alternatively, a two piece fastening system can be used based on clamps, pins or studs. Representatives of suitable attachment means are those described in U.S. Pat. Nos. 3,184,874, 3,260,007, 3,595,201, 3,388,492 and 3,942,480. A particularly preferred attachment means when the insect control device is prepared in the preferred ear tag form is the attachment means described in U.S. Pat. No. 3,731,414.

The present invention and its benefits are further described in the following examples, which are intended only to be illustrative of the invention, and should not be construed as limiting.

EXAMPLE 1

Insect control devices in accordance with invention in the form of ear tags containing 8%w alpha-cyano-3-phenoxybenzyl-alphaisopropyl-4-chlorophenyl acetate insecticide (about 23%w of which comprises the stereoisomer(−)-S-alpha-cyano-3-phenoxybenzyl(+)-S-alpha-isopropyl-p-chlorophenyl acetate), 28%w of dioctyl adipate plasticizer, and 61%w of polyvinyl chloride (PVC) and 3.0%w of a PVC stabilizer were prepared by mixing the liquid ingredients (the insecticide, plasticizer and stabilizer) with the PVC powder and heating the resultant mixture until a dry free-flowing powder (dry blend) was obtained. The dry blend was fed into the hopper of an injection molding machine where it was heated to a melt state, mixed until it was homogeneous and then forced into die cavities having the preferred ear tag configuration, after which it was cooled to yield the solid insecticide-containing ear tag.

EXAMPLE 2

Ear tags prepared in a manner similar to those made in Example 1 were tested for efficacy against face flies and horn flies on cattle at a university testing station. The ear tags were attached to the ears of a herd of 25 steers using the attachment means and applicator described in U.S. Pat. Nos. 3,731,414 and 3,812,859, respectively. After tagging the cattle were placed on a 20 acre pasture for six weeks and then moved to a 40 acre pasture for the remainder of the test. One week prior to tagging and weekly thereafter face and horn fly counts were taken daily on ten randomly selected tagged cattle. Untreated cattle for the experiment consisted of a herd of 19 steers and heifers of comparable size which were located within the vicinity of the tagged cattle. The results obtained from these tests are shown in Tables I and II below.

TABLE I

EFFICACY AGAINST HORN FLIES ON CATTLE

Fly Numbers and % Reduction Weeks After Treatment

| | −1 | 1 | 2 | 3 | 4 | 5 | 6 | 7 | 8 | 9 | 10 |
|---|---|---|---|---|---|---|---|---|---|---|---|
| TREATED | | | | | | | | | | | |
| 1 | 150 | 0 | 0 | 0 | 0 | 0 | 0 | 0 | 0 | 0 | 0 |
| 2 | 500 | 0 | 0 | 0 | 0 | 0 | 0 | 0 | 0 | 0 | 0 |
| 3 | 300 | 0 | 0 | 0 | 0 | 0 | 0 | 0 | 0 | 0 | 0 |
| 4 | 150 | 0 | 0 | 0 | 0 | 0 | 0 | 0 | 0 | 0 | 0 |
| 5 | 200 | 0 | 0 | 0 | 0 | 0 | 0 | 0 | 0 | 0 | 0 |
| 6 | 300 | 0 | 0 | 0 | 0 | 0 | 0 | 0 | 0 | 0 | 0 |
| 7 | 400 | 0 | 0 | 0 | 0 | 0 | 0 | 0 | 0 | 0 | 0 |
| 8 | 300 | 0 | 0 | 0 | 0 | 0 | 0 | 0 | 0 | 0 | 0 |
| 9 | 175 | 0 | 0 | 0 | 0 | 0 | 0 | 0 | 0 | 0 | 0 |
| 10 | 500 | 0 | 0 | 0 | 0 | 0 | 0 | 0 | 0 | 0 | 0 |
| TOTAL | 2975 | 0 | 0 | 0 | 0 | 0 | 0 | 0 | 0 | 0 | 0 |
| AVERAGE | 297.5 | 0 | 0 | 0 | 0 | 0 | 0 | 0 | 0 | 0 | 0 |
| % REDUCTION | — | 100 | 100 | 100 | 100 | 100 | 100 | 100 | 100 | 100 | 100 |
| UNTREATED | | | | | | | | | | | |
| 1 | 400 | 300 | 600 | 200 | 300 | 1000 | 600 | 150 | 150 | 500 | 200 |
| 2 | 500 | 200 | 800 | 150 | 300 | 200 | 300 | 200 | 200 | 400 | 125 |
| 3 | 800 | 150 | 200 | 300 | 200 | 600 | 800 | 300 | 300 | 100 | 400 |
| 4 | 100 | 200 | 600 | 200 | 600 | 600 | 500 | 300 | 300 | 250 | 250 |
| 5 | 600 | 400 | 1000 | 300 | 400 | 500 | 400 | 250 | 75 | 100 | 300 |
| 6 | 400 | 100 | 500 | 400 | 300 | 300 | 100 | 200 | 400 | 75 | 300 |
| 7 | 1000 | 300 | 800 | 100 | 400 | 400 | 300 | 500 | 400 | 300 | 200 |
| 8 | 200 | 100 | 500 | 300 | 100 | 800 | 200 | 400 | 600 | 400 | 150 |
| 9 | 800 | 300 | 800 | 250 | 300 | 500 | 400 | 500 | 600 | 75 | 175 |
| 10 | 800 | 200 | 400 | 300 | 200 | 300 | 600 | 300 | 225 | 300 | 150 |
| TOTAL | 5600 | 2250 | 6200 | 2500 | 3100 | 5200 | 4200 | 3100 | 3250 | 2500 | 2250 |
| AVERAGE | 560.0 | 225.0 | 620.0 | 250.0 | 310.0 | 520.0 | 420.0 | 310.0 | 325.0 | 250.0 | 225.0 |

TABLE II

EFFICACY AGAINST FACE FLIES ON CATTLE

Fly Numbers and % Reduction Weeks After Treatment

| | −1 | 1 | 2 | 3 | 4 | 5 | 6 | 7 | 8 | 9 | 10 |
|---|---|---|---|---|---|---|---|---|---|---|---|
| TREATED | | | | | | | | | | | |
| 1 | 15 | 8 | 0 | 6 | 1 | 4 | 10 | 16 | 4 | 10 | 3 |
| 2 | 25 | 8 | 1 | 3 | 3 | 4 | 14 | 9 | 9 | 12 | 1 |
| 3 | 25 | 6 | 6 | 0 | 1 | 10 | 9 | 10 | 10 | 8 | 8 |
| 4 | 20 | 4 | 3 | 1 | 0 | 9 | 6 | 4 | 4 | 6 | 0 |
| 5 | 35 | 10 | 1 | 0 | 1 | 7 | 14 | 5 | 5 | 5 | 3 |
| 6 | 20 | 12 | 0 | 0 | 0 | 5 | 7 | 12 | 11 | 9 | 4 |
| 7 | 17 | 2 | 0 | 0 | 0 | 3 | 12 | 7 | 3 | 11 | 4 |
| 8 | 24 | 6 | 0 | 0 | 1 | 0 | 9 | 12 | 8 | 14 | 4 |
| 9 | 20 | 11 | 3 | 0 | 0 | 5 | 8 | 16 | 16 | 8 | 0 |
| 10 | 15 | 9 | 0 | 0 | 0 | 9 | 13 | 5 | 6 | 14 | 5 |
| TOTAL | 216 | 76 | 14 | 10 | 7 | 56 | 102 | 96 | 76 | 97 | 31 |
| AVERAGE | 21.6 | 7.6 | 1.4 | 1.0 | .7 | 5.6 | 10.2 | 9.6 | 7.6 | 9.7 | 3.1 |
| % REDUCTION | — | 72 | 91 | 95 | 96 | 77 | 69 | 58 | 67 | 48 | 63 |
| UNTREATED | | | | | | | | | | | |
| 1 | 20 | 20 | 20 | 40 | 12 | 25 | 30 | 25 | 8 | 25 | 9 |
| 2 | 25 | 35 | 12 | 19 | 20 | 20 | 25 | 14 | 30 | 16 | 10 |
| 3 | 11 | 30 | 25 | 16 | 25 | 25 | 45 | 20 | 20 | 20 | 11 |
| 4 | 15 | 40 | 20 | 14 | 16 | 15 | 25 | 16 | 15 | 12 | 6 |
| 5 | 12 | 20 | 16 | 12 | 13 | 30 | 40 | 25 | 20 | 22 | 5 |
| 6 | 15 | 25 | 14 | 25 | 20 | 35 | 35 | 30 | 25 | 8 | 8 |
| 7 | 10 | 15 | 3 | 22 | 35 | 25 | 20 | 35 | 20 | 14 | 8 |
| 8 | 5 | 30 | 12 | 14 | 10 | 20 | 35 | 12 | 18 | 30 | 4 |
| 9 | 11 | 20 | 10 | 10 | 8 | 30 | 50 | 40 | 25 | 25 | 10 |

TABLE II-continued
EFFICACY AGAINST FACE FLIES ON CATTLE

| | Fly Numbers and % Reduction Weeks After Treatment | | | | | | | | | | |
|---|---|---|---|---|---|---|---|---|---|---|---|
| | −1 | 1 | 2 | 3 | 4 | 5 | 6 | 7 | 8 | 9 | 10 |
| 10 | 21 | 35 | 20 | 23 | 18 | 22 | 20 | 25 | 30 | 15 | 7 |
| TOTAL | 145 | 270 | 152 | 195 | 177 | 247 | 325 | 242 | 211 | 187 | 78 |
| AVERAGE | 14.5 | 27.0 | 15.2 | 19.5 | 17.7 | 24.7 | 32.5 | 24.2 | 21.1 | 18.7 | 7.8 |

EXAMPLE 3

Ear tags similar to those employed in Example 2 were employed in a series of tests conducted at another university station to determine their efficacy against Gulf Coast ticks and horn flies. In the test against ticks, a herd of 31 experimental cattle of mixed breed were divided into two groups of 15 and 16 animals, repsectively. The group of 15 animals was fitted with an ear tag in each ear while the 16 animal group was untreated and served as a control. The number of ticks attaching to the ears of the animals were counted on the treated and untreated animals at the time intervals shown in Table III.

TABLE III
Efficacy Against Ticks

| | Number of Ticks Per Animal | |
|---|---|---|
| Time Interval | Treated | Untreated |
| Preatment | 8.6 | 12.3 |
| 6 days | 0.6 | 8.4 |
| 14 days | 0.7 | 10.6 |
| 27 days | 0.4 | 5.8 |
| 47 days | 0.1 | 75.0 |
| 54 days | 0.9 | 4.4 |

Horn fly counts were made on the same animals treated as described above. The number of flies indicated in Table IV below is the total body estimate. The untreated herd to which the above herd was compared consisted of 16 cows and 11 cross-bred calves in an adjacent enclosure.

TABLE IV
Efficacy Against Horn Flies

| | Horn Flies Per Animal | |
|---|---|---|
| Time Interval | Treated | Untreated |
| Preatment | 325 | 175 |
| 6 days | 25 | 175 |
| 14 days | 20 | 225 |
| 27 days | 10 | 350 |
| 39 days | 5 | 475 |
| 46 days | 7 | 800 |
| 80 days | 120 | 2500 |
| 88 days | 7 | 5000 |
| 96 days | 5 | 3000 |
| 102 days | 5 | 2500 |

EXAMPLE 4

The stability to evaporative loss of the insecticide-containing plasticized PVC compositions employed in the present insect control devices was determined by placing 0.1 inch thick injection molded slabs of the composition in an oven at 130° F. for various intervals after which the slabs were analyzed for insecticide (alpha-cyano-3-phenoxybenzyl-alpha-isopropyl-4-chlorophenyl acetate) and plasticizer (dioctyladipate) content with the results shown in Table V.

TABLE V

| | Concentration, % w | |
|---|---|---|
| Sample Age | Insecticide | Plasticizer |
| Initial | 9.6 | 29.3 |
| One Month | 9.5 | 29.0 |
| Four Months | 9.2 | 29.0 |

The foregoing data illustrate that neither the insecticide nor the plasticizer are lost in any significant amounts during prolonged exposure at 130° F., which is considerably higher than the normal temperature of cows or other livestock. From this data it is evident that the surprising efficacy of the present compositions is not due to nor predictable from the evaporative characteristics of the compositions employed in the present insect control devices.

EXAMPLE 5

Injection molded slabs 0.1 inch thick of the composition of Example 1 were stored in a polyethylene bag for a period of eighteen months, after which the surfaces were examined under a microscope using polarized incident light at about 120 diameters magnification. No evidence was detected of any crystallinity of the insecticide on the surface of the composition. Therefore it is evident that the surprising efficacy of the present compositions is not due to crystallization of insecticide from the polymeric resin matrix as in the case of other prior art activators.

It is to be understood that the foregoing detailed description of the invention is merely given by way of illustration, and that many variations may be made without departing from the spirit or scope of the invention.

What is claimed is:

1. An insect control device for attachment to cattle or other livestock comprising:
   (a) a polymeric resin matrix having dispersed therein an insectically effective amount of a liquid, insecticidally-active isomer of alpha-cyano-3-phenoxybenzyl-alpha-isopropyl-4-chlorophenyl acetate, and
   (b) an attachment means for affixing said polymeric resin matrix to said animal.

2. The insect control device of claim 1 wherein the polymeric resin matrix is formed from a plasticized thermoplastic resin.

3. The insect control device of claim 2 wherein the plasticizer is an ester of a polybasic carboxylic acid.

4. The insect control device of claim 3 wherein the thermoplastic resin is a polyvinyl halide resin.

5. The insect control device of claim 4 wherein the plasticizer is dioctyl adipate or dioctyl phthalate.

6. The insect control device of claim 5 wherein the thermoplastic resin is polyvinyl chloride.

7. The insect control device of claim 6 in the form of a tag which is attachable to the ear of said animal.

8. The insect control device of claim 7 wherein the thermoplastic resin is present in the amount of from about 35 to about 75 percent by weight of the total composition, the amount of plasticizer is present in the amount of from 10 to 45 percent by weight of the total composition and the insecticide is present in the amount of 1 to 20 percent by weight of the total composition.

9. The insect control device of claim 8 wherein the insecticide utilized contains at least 10 percent by weight of the stereoisomer(−)-S-alpha-cyano-3-phenoxybenzyl(+)-S-alpha-isopropyl-4-chlorophenyl acetate.

10. A method for controlling insects on cattle and other livestock which comprises attaching to said animal a polymeric resin matrix containing an insecticidally effective amount of a liquid, insecticidally-active isomer of alpha-cyano-3-phenoxybenzyl-alpha-isopropyl-4-chlorophenyl acetate.

11. The method of claim 10 wherein the polymeric resin matrix is shaped in the form of an ear tag and is attached to the ear of said animal.

* * * * *